US010794918B2

(12) United States Patent
Curdt et al.

(10) Patent No.: US 10,794,918 B2
(45) Date of Patent: Oct. 6, 2020

(54) USE OF GFAP FOR IDENTIFICATION OF INTRACEREBRAL HEMORRHAGE

(71) Applicants: Matthias Sitzer, Bad Oeynhausen (DE); Christian Foerch, Hofheim (DE)

(72) Inventors: Ingo Curdt, Hochheim am Main (DE); Matthias Sitzer, Dreieich (DE); Christian Foerch, Hofheim (DE)

(73) Assignees: Matthias Sitzer, Herford (DE); Christian Foerch, Hofheim (DE)

( * ) Notice: Subject to any disclaimer, the term of this patent is extended or adjusted under 35 U.S.C. 154(b) by 602 days.

(21) Appl. No.: 14/711,228

(22) Filed: May 13, 2015

(65) Prior Publication Data

US 2015/0247867 A1    Sep. 3, 2015

Related U.S. Application Data

(63) Continuation of application No. 11/388,156, filed on Mar. 23, 2006, now abandoned, which is a continuation of application No. PCT/EP2004/010711, filed on Sep. 24, 2004.

(30) Foreign Application Priority Data

Sep. 24, 2003 (EP) .................................... 03021571

(51) Int. Cl.
*G01N 33/68* (2006.01)
(52) U.S. Cl.
CPC ..... *G01N 33/6896* (2013.01); *G01N 33/6893* (2013.01); *G01N 2800/2871* (2013.01)
(58) Field of Classification Search
None
See application file for complete search history.

(56) References Cited

U.S. PATENT DOCUMENTS

| | | | |
|---|---|---|---|
| 4,743,542 A | 5/1988 | Graham, Jr. et al. | |
| 5,380,650 A * | 1/1995 | Barnard | C12Q 1/28 435/28 |
| 5,733,721 A | 3/1998 | Hemstreet, III et al. | |
| 5,750,345 A | 5/1998 | Bowie | |
| 6,235,489 B1 | 5/2001 | Jackowski | |
| 6,449,562 B1 | 9/2002 | Chandler et al. | |
| 7,144,708 B2 | 12/2006 | Janigro et al. | |
| 7,291,495 B2 | 11/2007 | Benjanin et al. | |
| 7,371,582 B2 | 5/2008 | Nahm et al. | |
| 7,396,654 B2 | 7/2008 | Hayes et al. | |
| 7,396,689 B2 | 7/2008 | Dowd et al. | |
| 2002/0147998 A1 | 10/2002 | McConlogue et al. | |
| 2003/0119064 A1 | 6/2003 | Valkirs et al. | |
| 2003/0129134 A1 | 7/2003 | Chenard et al. | |
| 2003/0199000 A1 | 10/2003 | Valkirs et al. | |
| 2004/0121343 A1 | 6/2004 | Buechler et al. | |
| 2004/0203083 A1 | 10/2004 | Buechler et al. | |
| 2004/0253637 A1 | 12/2004 | Buechler et al. | |
| 2005/0112585 A1 | 5/2005 | Zichi et al. | |
| 2006/0240480 A1 | 10/2006 | Curdt et al. | |
| 2011/0143375 A1 | 6/2011 | Wang et al. | |
| 2017/0045534 A1 | 2/2017 | Wang et al. | |

FOREIGN PATENT DOCUMENTS

| | | | |
|---|---|---|---|
| EP | 0186799 A1 | 7/1986 | |
| EP | 1310797 A2 | 5/2003 | |
| EP | 1 519 194 | 3/2005 | |
| WO | 2003/016910 A1 | 2/2003 | |
| WO | WO-03062824 A1 * | 7/2003 | ............ B01L 3/5023 |
| WO | 2004/059293 A2 | 7/2004 | |
| WO | WO-04/078204 | 9/2004 | |
| WO | WO-05/029087 | 3/2005 | |
| WO | WO-05/029088 | 3/2005 | |

OTHER PUBLICATIONS

ECC Guidelines, "Part 7: The Era of Reperfusion, Section 2: Acute Stroke", Circulation 2000;102(suppl I):I-204-I-216, https://doi.org/10.1161/01.CIR.102.suppl_1.I-204 (Year: 2000).*
Hesselink, "Imaging of Stroke and Cerebral Ischemia", Aug. 2003, 9 pages, retrieved from https://web.archive.org/web/20030826111030/http://spinwarp.ucsd.edu/neuroweb/Text/br-710.htm on May 6, 2018 (Year: 2003).*
Albers, G. et al., "Transient Ischemic Attack—Proposal for a New Definition," N. Engl. J. Med., vol. 347, No. 21, Nov. 21, 2002, p. 1713-1716.
Duncan, P., et al., "Outcome Measures in Acute Stroke Trials: A Schematic Review and Some Recommendations to Improve Practice," Stroke, Jun. 2000, p. 1429-1438.
Dvorak et al., "Characterisation of the Diagnostic Window of Serum Glial Fibrillary Acidic Protein for the Differentiation of Intracerebral Haemorrhage and Ischaemic Stroke," Cerebrovasc Dis, 2009, vol. 27, p. 37-41.
Foerch et al., "Serum glial fibrillary acidic protein as a biomarker for intracerebral haemorrhage in patients with acute stroke," J Neurol Neurosurg Psychiatry, 2006, vol. 77, p. 181-184, doi:10.1136/jnnp.2005.074823.
Hayakawa, T. et al., "Astroprotein (GFAP) Levels in Cerebrospinal Fluid of Stroke Patients," Neurol Med Chir (Tokyo), 1984, vol. 24, p. 13-18.
Hermann, M. et al., "Release of Glial Tissue-Specific Proteins After Acute Stroke: A Comparative Analysis of Serum Concentrations of Protein S-100B and Glial Fibrillary Acidic Proteins," Stroke, Nov. 2000, p. 2670-2677.
Mair, Johannes et al., "Cardiac Troponin T in the Diagnosis of Myocardial Injury," Critical Reviews in Clinical Laboratory Sciences, 1992, vol. 29, No. 1, p. 31-57.
Mao, S., et al., "Electrochemiluminescence assay for basic carboxypeptidases: inhibition of basic carboxypeptidases and activation of thrombin-activated fibrinolysis inhibito," Analytical Biochemistry, 2003, vol. 319, p. 159-170.

(Continued)

*Primary Examiner* — Christine Foster
(74) *Attorney, Agent, or Firm* — Morrison & Foerster LLP

(57) ABSTRACT

The present invention relates to the use of glial fibrillary acidic protein (GFAP) as a diagnostic marker for intracerebral hemorrhage. The invention especially relates to methods for the early detection of intracerebral hemorrhage. Such early and rapid detection can be performed rapidly e.g. by a test strip format assay. GFAP can be used as a stand-alone marker or in combination with one or more other markers.

5 Claims, 2 Drawing Sheets

(56) References Cited

OTHER PUBLICATIONS

Matsubara, S. and Takamori, M., "Experimental allergic myositis: ultrastructural histochemical, immunological and immunohistochemical studies," Acta Neuropathologica (Berl), 1987, No. 74, p. 151-157.

Mc Comb, Robert B. and Bowers, George N., Jr., "Alkaline Phosphatse," 1979, Plenum Press, New York, Bibliography pages only (two pages total).

Missler et al., "Measurement of glial fibrillary acidic protein in human blood: analytical method and preliminary clinical results," Clin Chem, 1999, vol. 45, p. 138-141.

Mohideen, M. R., "Brain natriuretic peptide is more than a marker," Ceylon Medical Journal, Sep. 2002, vol. 47, No. 3, p. 81-82.

Niebro-Dobosz, I. et al., "Immunochemical analysis of some proteins in chrebrospinal fluid and serum of patients with ischemic strokes," Folia Neuropathol, 1994, vol. 32, No. 3, p. 129-137.

Okazaki, Taku and Honjo, Tasuku, "Pathogenic roles of cardiac autoantibodies in dilated cardiomyopathy," Trends in Molecular Medicine, Jul. 2005, vol. 11, No. 7, p. 322-326.

"Recommendations of the German Society for Clinical Chemistry," Z. klin. Chem u klin. Biochem., 1972, vol. 10, p. 182-192.

Roche, Instruction Manual for "DIG Detection ELIS (ABTS)" and "DIG Detection ELISA (TMB)", Version 2, Nov. 1999, retrieved from http://jenobiotech.com/techsupport/Protocol/ELISA1-17.pdf on Apr. 25, 2014, 18 pages.

Turner, C. et al., "Expression of COX2, HO1, and GFAP following Collagenase-induced intracerebral hemorrhage," Neurology, 2000, vol. 54, p. A299.

Van Geel, et al., "Measurement of glial fibrillary acidic protein in blood: an analytical method," Clinica Chimica W. Acta, 2002, vol. 326, p. 151-154.

Walker et al., DNA-based molecular diagnostic techniques: research needs for standardization and validation of the detection of aquatic animal pathogens and diseases. Report and proceedings of the Joint FAO/NACA/CSIRO/ACIAR/FDID Expert Workshop. Bangkok, Thailand, Feb. 7-9, 1999. FAO Fisheries Technical Paper No. 395 Rome, FAO, 2000, pp. i-iv & 30-37.

Yang, H. et al., "Electrochemiluminescence: A New Diagnostics and Research Tool," Bio/Technology, Feb. 1994, vol. 12, p. 193-194.

Zhang et al., "Expression of glial fibrillary acidic protein in peri-cerebral hemorrhage foci," journal of the Fourth Military Medical University (Di-si Junyl Daxue Xuebao), Sep. 15, 2003, vol. 24, No. 17, p. 1586-1588.

Zwieg, M. et al., "Receiver-Operating Characteristic (ROC) Plots: A Fundamental Evaluation Tool in Clinical Medicine," Clin. Chem., 1993, vol. 39, No. 4, p. 561-577.

Chekhonin et al., "Enzyme immunoassay of antibodies to neurospecific proteins in examination of blood-brain barrier function," Immunologiya (1996) 0(2):67-69.

Lamers et al., "Protein S-100b, Neuron-Specific Enolase (NSE), Myelin Basic Protein (MBP) and Glial Fibrillary Acidic Protein (GFAP) in Cerebrospinal Fluid (CSF) and Blood of Neurological Patients," Brain Res Bull (2003) 61(3): 261-264.

Pelinka et al., "Glial Fibrillary Acidic Protein in Serum After Traumatic Brain Injury and Multiple Trauma," J Trauma (2004) 57(5):1006-1012.

Petzold et al., "An ELISA for glial fibrillary acidic protein." J Immunol Methods (2004) 287(12):169-177.

Vos et al., "Glial and neuronal proteins in serum predict outcome after severe traumatic brain injury," Neurology (2004) 62(8):1303-1310.

\* cited by examiner

USE OF GFAP FOR IDENTIFICATION OF INTRACEREBRAL HEMORRHAGE

CROSS REFERENCE TO RELATED APPLICATIONS

This application is a continuation of U.S. application Ser. No. 11/388,156 filed Mar. 23, 2006 (now abandoned), which is a continuation of International Application No. PCT/EP2004/010711 filed Sep. 24, 2004, which claims priority to European Application No. 03021571.9 filed Sep. 24, 2003, the disclosures of which are hereby incorporated in their entirety.

FIELD OF THE INVENTION

The present invention relates to the use of serum glial fibrillary acidic protein (GFAP) as a diagnostic marker for intracerebral hemorrhage. The invention especially relates to methods for the very early assessment of intracerebral hemorrhage. Such early and rapid detection can be immediately performed e.g. by a test strip format assay. GFAP can be used as a stand-alone marker or in combination with one or more other markers.

BACKGROUND OF THE INVENTION

Stroke is a manifestation of vascular injury to the brain which is commonly secondary to arteriosclerosis or cardiac disease, and is the third leading cause of death (and the second most common cause of neurological disability) in the United States.

Stroke can be categorized into two major types, "ischemic stroke" and "hemorrhagic stroke".

Ischemic smoke encompasses thrombotic, embolic, lacunar and hypo perfusion types of strokes. Thrombi are occlusions of arteries created in situ within the brain, while emboli are occlusions caused by material from a distant source, such as the heart or major vessels. Less frequently, thrombi may also result from vascular inflammation due to disorders such as meningitis or autoimmune vasculitis. Thrombi or emboli can result from atherosclerosis or other disorders, for example, arteritis, and lead to physical obstruction of arterial blood supply to the brain. Lacunar stroke refers to an infarct within sub-cortical regions of the brain.

The onset of ischemic stroke is often abrupt, and can become an "evolving stroke" manifested by neurological deficits that worsen over a 24-48 hour period. In evolving stroke, symptoms commonly include unilateral neurological dysfunction which extends progressively, without producing headache or fever. Evolving stroke may also become a "completed stroke," in which symptoms develop rapidly and are maximal within a few minutes.

A "transitory ischemic attack" is defined as a short-lasting (<24 hours, mostly less than 1 hour) focal neurological or neuropsychological symptom caused by a rapidly dissolving occlusion of a brain supplying artery by an embolus, (Albers G. W., et al.; TIA Working Group, "Transient ischemic attack proposal for a new definition", N. Engl. J. Med. 347 (2002) 1713-1716).

In contrast to ischemic stroke, hemorrhagic stroke is caused by intracerebral hemorrhage, i.e., bleeding into brain tissue, following blood vessel rupture within the brain. Intracerebral hemorrhage is typically due to chronic hypertension, and a resulting rupture of an arteriosclerotic vessel. Symptoms of intracerebral hemorrhage are abrupt, sometimes with the onset of headache and steadily increasing neurological deficits. Nausea, vomiting, delirium, seizures and loss of consciousness can occur. Nevertheless, in most cases neurological symptoms of patients with intracerebral hemorrhage are similar to patients with ischemic stroke.

Patients with head trauma must not be included in any group of stroke patients.

As described above, stroke is a pathological condition with acute onset that is caused by the occlusion or rupture of a blood vessel. As a consequence of vessel occlusion supply with oxygen and nutrients to the brain is blocked or severely reduced. The immediate area of injury is referred to as the "core," which contains brain cells that have died as a result of ischemia or physical damage. The "penumbra" is composed of brain cells that are neurologically or chemically connected to cells in the core. Cells within the penumbra are injured, but still have the ability to completely recover following removal of the insult caused during stroke. However, as ischemia or bleeding from hemorrhage continues, the core of dead cells can expand from the site of insult, resulting in a concurrent expansion of cells in the penumbra. The initial volume and rate of core expansion is related to the severity of the stroke and, in most cases, neurological outcome.

The brain contains two major types of cells, neurons and glial cells. Neurons are the most important cells in the brain, and are responsible for maintaining communication within the brain via electrical and chemical signaling. Glial cells function mainly as structural components of the brain, and they are approximately 10 times more abundant than neurons. Glial cells of the central nervous system (CNS) are astrocytes and oligodendrocytes.

Cell death during stroke occurs as a result of ischemia or physical damage to the cells of the CNS. During ischemic stroke, an infarct occurs, greatly reducing or stopping blood flow beyond the site of vessel occlusion. The zone immediately beyond the infarct soon lacks suitable blood concentrations of the nutrients essential for cell survival. Cells that lack nutrients essential for the maintenance of important functions like metabolism soon die. Hemorrhagic stroke can induce cell death by direct trauma, elevation in intracranial pressure, and the release of damaging biochemical substances in blood. When cells die, they release their cytosolic contents into the extracellular milieu.

The barrier action of tight junctions between capillary endothelial cells, the basal lamina and astrocytes is referred to as the "blood-brain barrier". This barrier is normally impermeable to proteins and other molecules, both large and small.

Substances that are secreted by the neurons and glial cells (intracellular brain compartment) of the CNS can freely pass into the extracellular milieu (extracellular brain compartment). Likewise, substances from the extracellular brain compartment can pass into the intracellular brain compartment. The passage of substances between the intracellular and extracellular brain compartments are restricted by the normal cellular mechanisms that regulate substance entry and exit.

Substances that are found in the extracellular brain compartment also are able to pass freely into the cerebrospinal fluid, and vice versa. This movement is controlled by diffusion.

The movement of substances between the vasculature (i.e., systemic circulation) and the CNS is restricted by the blood-brain barrier.

Depending upon their size, specific markers of cerebral injury that are released from injured brain cells during stroke or other cerebral injuries will only be found in peripheral blood when CNS injury is coupled with or followed by an increase in the permeability of the blood brain barrier. This is particularly true for larger molecules.

To date there is the concurrent opinion in the scientific community that, except for damages caused by severe head trauma, specific markers of cerebral injury will only be present in peripheral blood if there has been a sufficient increase in the permeability of the blood-brain barrier that allows these large molecules to diffuse across.

Current diagnostic methods for stroke include costly, time-consuming or invasive procedures such as noncontrast computed tomography (CT) scan, magnetic resonance imaging (MRI), or intra-arterial angiography. Determining the immediate cause of stroke and differentiating ischemic from hemorrhagic stroke is difficult. CT scans can detect parenchymal bleeding greater than 1 $cm^3$ and 95% of all subarachnoid hemorrhages. CT scan often cannot detect ischemic strokes until 6-12 hours from onset, depending on the infarct size. MRI may be more effective than CT scan in early detection of ischemic stroke, but it is less accurate at differentiating ischemic from hemorrhagic stroke, and is not widely available. Angiography is a definitive test to identify stenosis or occlusion of large and small cranial blood vessels, and can locate the cause of subarachnoid hemorrhages, define aneurysms, and detect cerebral vasospasm. It is, however, an invasive procedure that is also limited by cost and availability.

Immediate correct classification of the underlying type of stroke in a patient experiencing stroke can be critical. For example, tissue plasminogen activator (TPA) given within three hours of symptom onset in ischemic stroke is beneficial for selected acute stroke patients. In contrast, thrombolytics and anticoagulants are strongly contraindicated in hemorrhagic strokes.

Thus, early differentiation of ischemic events from hemorrhagic events is imperative. Moreover, delays in the identification of stroke type limit the number of patients that may benefit from early intervention and appropriate therapy.

Ideally such early indication for intracerebral hemorrhage as cause of the symptoms would be brought about by a biochemical marker which can be analyzed from a test sample obtained from the subject affected. Most convenient such analysis method should allow to perform the analysis, especially in cases of emergency not only in the central lab but also right next to the patient, e.g., whilst transporting a patient to the emergency department of a hospital.

A marker, which is useful in differentiation of intracerebral hemorrhage from other types of stroke or TIAs, has to be very specific for intracerebral hemorrhage, because false classification might result in a not adequate treatment. Such marker ideally would not be present or only be present in rather a low concentration in a test sample taken from patients with an ischemic stroke or suffering from a TIA. And on the other hand such marker would be elevated in a high percentage of test samples taken from patients with hemorrhagic stroke.

Recently published WO 03/016910 relates to methods for diagnosis and evaluation of stroke and transient ischemic attacks. It especially relates to analysis of a patient sample for the presence or amount of a panel of markers. No individual marker specific for hemorrhagic stroke is discussed or disclosed.

Glial fibrillary acidic protein (GFAP) is a 55 kDa cytosolic protein that is a major structural component of astroglial filaments and is the major intermediate filament protein in astrocytes. GFAP is specific to astrocytes, which are interstitial cells located in the CNS and can be found near the blood-brain barrier.

Recent reports from researchers investigating serum GFAP levels and their associatiation with stroke are severely limited by the methods used, and have produced controversial results.

Niebroj-Dobosz, I., et al., in Folia Neuropathol. 32 (1994) 129-137, report that GFAP is not normally detected in serum. More recent investigations, on the contrary, report that GFAP would be present in about 30% of healthy blood donors (e.g., van Geel, W. et al., Clinica Chmica Acta 326 (2002) 151-154).

The release of GFAP after stroke has been also investigated recently. Herrmann M. et al., Stroke 31 (2000) 2670-2677, report that at the time of admission to the hospital 39% of their patients were found to have elevated levels of GFAP. They also found significantly increased levels of GFAP in patients with lacunar stroke.

Accordingly, there is an substantial need in the art for a rapid, sensitive and specific diagnostic assay for intracerebral hemorrhage. Such a diagnostic assay would greatly increase the number of patients that can receive beneficial stroke treatment and therapy, and reduce the costs associated with incorrect stroke diagnosis/classification.

It has now been found that the presence or the level of GFAP in a test sample obtained from a subject is extremely valuable in assessing the presence or absence of hemorrhagic stroke.

SUMMARY OF THE INVENTION

The present invention relates to a method of assessing the presence, absence or severity of intracerebral hemorrhage, said method comprising: analyzing a test sample obtained from a subject for the presence or amount of GFAP and correlating the presence or amount of GFAP in said sample to the presence, absence or severity of intracerebral hemorrhage. The methods and compositions described herein can meet the need in the art for rapid, sensitive and specific diagnostic assay to be used in the diagnosis and differentiation of intracerebral hemorrhage from various other forms of stroke and TIAs The present invention also relates to a test kit for performing the analysis for GFAP as well as to marker panels comprising the marker GFAP and one or more additional markers used in the differentiation of intracerebral hemorrhage from other types of stroke.

DETAILED DESCRIPTION OF THE INVENTION

Figure 1:
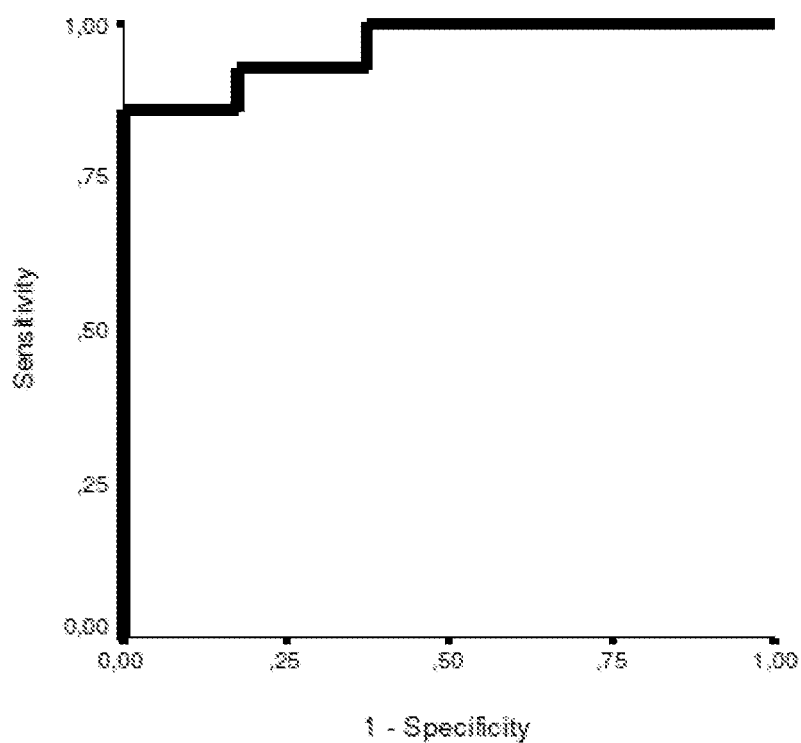
FIG. 1: ROC-analysis for 54 patients with moderate to severe neurological deficits after stroke. Receiver operating characteristic (ROC) (n=54) analysis revealed that a GFAP concentration of 3 pg/ml corresponds to a cut off value with highest sensitivity and specificity.

Correct classification of intracerebral hemorrhage versus other types of stroke or TIAs is crucial for aiding the physician to select the most appropriate mode of treatment. The investigators of the present invention could establish that GFAP can be used as a marker, aiding in differentiation of intracerebral hemorrhage from other types of stroke or TIAs. The presence or level of GFAP may for example aid the physician to timely choose CT-scans to further analyze and establish the type of stroke in an affected patient.

In a preferred embodiment the present invention therefore relates to the use of GFAP for assessing the presence, absence, or severity of intracerebral hemorrhage from a test sample, said method comprising: analyzing a test sample obtained from a subject for the presence or amount of GFAP and correlating the presence or amount of GFAP in said sample to the presence, absence or severity intracerebral hemorrhage.

Also preferred the present invention relates to the use of GFAP for assessing the presence or absence of intracerebral hemorrhage from a test sample, said method comprising: analyzing a test sample obtained from a subject for the presence or amount of GFAP and correlating the presence or amount of GFAP in said sample to the presence or absence of intracerebral hemorrhage.

The term "GFAP" as used herein must not be understood as implying only the full length molecule. It rather also refers to any physiological fragment or modification thereof, in particular, to immunologically detectable fragments.

The term "test sample" as used herein refers to a sample of bodily fluid obtained for the purpose of diagnosis, prognosis, or evaluation of a subject of interest, such as a patient. Test samples include blood, serum, plasma, cerebrospinal fluid, urine and saliva. Preferred test samples are blood, serum and plasma, with whole blood representing the most preferred sample.

The term "correlating," as used herein relates to comparing the presence or amount of GFAP in a test sample obtained from a patient with stroke to the statistical likelihood for presence, absence or severity of intracerebral hemorrhage. In preferred embodiments, the presence or the amount of GFAP is correlated to a global probability for presence or absence, for severity, or for a particular outcome, respectively, using ROC curves. Alike to any other diagnostic method applied in clinical diagnosis the GFAP-value alone is not decisive but will aid the physician in establishing a correct diagnosis.

Preferably the analysis of GFAP used for analyzing the test sample in a method according to the invention is performed by a specific GFAP-assay which does not detect a significant GFAP-level in samples obtained from healthy individuals. Using such assay for GFAP it could be established that GFAP, if measured by these appropriate means, can be used to differentiate between intracerebral hemorrhage and other types of stroke or TIAs. In a preferred embodiment the presence or absence of GFAP is correlated to the presence or absence of intracerebral hemorrhage, wherein a detectable level of GFAP is indicative for intracerebral hemorrhage.

The GFAP assay used in a method according to the present invention differs from the GFAP assays known in the art by having an improved sensitivity and less back-ground reaction. In a further preferred embodiment the method according to the present invention therefore is practiced using a specific GFAP assay for analysis of GFAP which has a lower limit of detection of 1 pg/ml, preferably this GFAP assay also yields a level of GFAP of less than 3 pg/ml in at least 95% of samples taken from healthy volunteers.

In a further preferred embodiment the present invention relates to a novel GFAP-assay itself, wherein said GFAP assay has a lower limit of detection of 3 pg/ml, more preferred of 1 pg/ml. Preferably the GFAP assay according to this invention does not detect a significant GFAP-level in healthy individuals, but detects measurable GFAP-levels in at least 60% of test samples obtained from patients with intracerebral hemorrhage. A non-significant level of GFAP is a level of GFAP at or below 3 pg/ml.

The preferred GFAP-assay according to the present invention has a clinical cut-off value of 3 pg/ml and yields no level of GFAP or a GFAP-level of less than this cut-off value in at least 95% of healthy volunteers.

As the skilled artisan appreciates absolute values, e.g., the cut-off value of 3 pg/ml, largely depend on standardization and assay procedures used and thus may be subject to change. A GFAP-assays based on a different standardization and thus giving different absolute values for GFAP concentration will not depart from the spirit if this invention as long as at least the diagnostic accuracy as assessed by ROC-analysis for this assay is obtained. The ROC-analysis is described in detail further below.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or intracerebral hemorrhage versus other types of stroke (dependent on the analysis in- or excluding TIAs).

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the curve (AUC) of the ROC plot. The area under the ROC curve is a measure of the probability that the perceived measurement will allow correct identification of a condition. By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Clinical utility of GFAP in a method according to the present invention has been assessed by receiver operator curve analysis (ROC; Zweig, M. H., and Campbell, G., Clin. Chem. 39 (1993) 561-577). It has been found in the whole patient population investigated that the AUC was 0.61.

A sub-group of patents showing a moderate to severe neurological deficit (a score of four and above, as assessed using the NIHSS classification, see e.g. Duncan P W, et al., "Outcome measures in acute stroke trials: a systematic review and some recommendations to improve practice." Stroke, 31 (2000) 1429-143) has been separately investigated. In this sub-set of patients the clinical sensitivity for intracerebral hemorrhage was 86% at a specificity of 100%. It also represents a preferred embodiment to use the inventive method in patients presenting with a moderate to severe neurological deficit.

A preferred GFAP assay capable of being used in a method according to the present invention has a specificity of at least 90% and a corresponding sensitivity of at least 75%, when calculated for the group of intracerebral hemorrhage patients versus all other stroke patients (including patients with TIA). As the person skilled in statistics will appreciate the numbers used for such analysis must be high enough to allow for significant conclusions to be drawn.

As the skilled artisan will appreciate now that the central role of GFAP for differentiating intracerebral hemorrhage from other types of stroke or TIA has been established it is likely that addition of other markers into a marker panel comprising GFAP may further aid and improve in the differentiation of intracerebral hemorrhage from other events. In a preferred embodiment the present invention relates to a method of diagnosing intracerebral hemorrhage in a subject, said method comprising: analyzing a test sample obtained from a subject for the presence or amount of GFAP as well as for the presence or absence of a marker indicative for ischemic stroke, wherein the presence of GFAP is indicative for the presence of intracerebral hemorrhage, whereas the absence of said marker for ischemic stroke is used to rule out ischemic stroke.

As the skilled artisan appreciates there are numerous ways to detect GFAP with the sensitivity and specificity described above. Preferably such detection is performed in a specific binding assay. Most preferred is a specific immunoassay for GFAP employing one or more antibody specifically binding thereto. Specific binding assays, especially immunoassays are described in detail in relevant textbooks (cf., e.g. Tijssen, P., Practice and theory of enzyme immunoassays 11 (1990) Elsevier, Amsterdam, or Diamandis, et al., eds. (1996) Immunoassay, Academic Press, Boston).

In clinical routine diagnostics frequently methods based on a heterogeneous immunoassay format are used. In a preferred embodiment according to the present invention the method for detection of GFAP is a competitive immunoassay.

Even more preferred are immunoassays according to the sandwich assay principle, in which an antibody-antigen-antibody complex, also called a sandwich is formed.

In a preferred embodiment according to the present invention the method for specific detection of GFAP is a sandwich immunoassay, wherein at least one antibody binding to the epitope bound by monoclonal antibody 4A11 (RDI: catalogue number GFAPabm-411) is used. Preferably the GFAP assay according to the present invention is based on a monoclonal antibody recognizing the same epitope as monoclonal antibody 4A11.

Preferably, such a sandwich method for determination of GFAP comprises the following steps:
(a) mixing of the sample with the first antibody to GFAP carrying a group suitable for binding to a solid phase or mixing the sample with the first GFAP-specific antibody which is already bound to a solid phase,
(b) mixing of this solution with a second antibody to GFAP binding to an epitope outside the epitope of the first antibody under conditions that a first antibody-GFAP-second antibody complex is formed,
(c) binding of the immune complex formed to a solid phase,
(d) separation of the solid phase from the liquid phase, and
(e) detection of the label in one or both phases.

In a quantitative determination the same measurement is carried out with a defined amount of GFAP as a standard and after the determination of the sample a step f) is performed, i.e. the measuring values of the standard or standard curve are compared to those obtained with the sample, and the corresponding concentration of GFAP is extrapolated.

The first antibody specific for GFAP can be bound directly to the solid phase or indirectly via a specific binding pair system. The direct binding of this antibody to the solid phase follows methods known to the expert, for example in an adsorptive way. If the binding is indirect via a specific binding pair system the first antibody is a conjugate consisting of an antibody against GFAP and a first partner of the specific binding pair system. A specific binding pair system means two partners which can react specifically with each other. This binding can be based on an immunological binding or on an alternative specific binding. Preferred combinations for such specific binding pair are biotin and anti-biotin, hapten and anti-hapten, Fc-fragment of an antibody and antibodies against this Fc-fragment or carbohydrate and lectin. Preferably, a combination of biotin and avidin or of biotin and streptavidin is used as a specific binding pair system.

The second partner of the specific binding pair system is coated to a solid phase. Streptavidin or avidin is used preferably. The binding of this partner of the specific binding pair system to an insoluble carrier material can be performed according to standard procedures known to the expert. Here a covalent as well as an adsorptive binding is suitable.

As a solid phase test tubes or microtiter plates made of polystyrene or similar plastics are suitable which are coated with the second partner of the specific binding pair system. Further suitable and particularly preferred are particulate substances such as latex particles, magnetic particles, molecular sieve materials, and glass corpuscles. Paper or nitrocellulose can also be used as carriers. Magnetic beads coated with the second partner of the specific binding pair system as described above are used particularly preferred. After completion of the immunological reaction and binding of the immunological complex formed to the solid phase, these microparticles can be separated from the liquid phase for example by filtration, centrifugation or in the case of the magnetic particles via a magnet. Detection of label bound to the solid phase (or of the label remaining in the liquid phase or of both) is then performed according to standard procedures.

The second antibody to GFAP, preferably binds to an epitope outside the first GFAP epitope, thus avoiding interference or competition with the first antibody.

Besides the so-called wet tests as described above, with test reagents in a liquid phase, all standard dry test formats suitable for the detection of antigens, haptens, peptides, proteins, antibodies etc. can be used too. These dry tests or test strips as for instance described in EP-A-0 186 799 combine all test components on one single carrier-except the sample to be analyzed.

As described further above rapid and early diagnosis is crucial for aiding in the classification of type of stroke, since patients suffering from different types of stroke are likely to profit from quite different modes and regimens of treatment. The need for both rapid and early diagnosis is best met by measurement of GFAP in a dry test format, e.g. in form of a strip test. In a preferred embodiment the present invention therefore relates to a method of assessing the presence, absence or severity of intracerebral hemorrhage from a test sample, said method comprising: analyzing a test sample obtained from a subject for the presence or amount of GFAP and correlating the presence or amount of GFAP in said sample to the presence, absence or severity of hemorrhagic stroke, wherein said analysis for GFAP is performed in a test strip assay format.

At test strip assay format has the great advantage that it can be used next to the patient, especially in cases of emergency.

A test strip assay is most conveniently designed to yield a qualitative result. If an analyte is present in a concentration at or above the lower limit of detection as set up in the test strip, a positive signal is obtained. Such negative or positive result as obtained by a test strip would than be indicative for the absence or presence of intracerebral hemorrhage, respectively.

It is also preferred, to apply a marker panel used to further improve the assessment of the presence or absence of intracerebral hemorrhage comprising GFAP and one or more markers to a test strip.

Armed with the technical progress described in the present invention the skilled artisan will have no problem in designing a GFAP assay with similar technical properties and intended clinical use as the one specifically described in the examples section. For example it now may well be possible to establish a more sensitive assay for GFAP. Such more sensitive assay may result in measurable levels of GFAP in healthy volunteers and a further improved assessment for presence or absence of intracerebral hemorrhage in an individual, without departing from the spirit of this invention.

In a further embodiment the present invention relates to a kit for measurement of GFAP in a sample comprising: one or more reagents for determining the presence or amount of GFAP and instructions for performing the assays to achieve said determining, wherein said kit has a lower limit of detection of 3 pg/ml. Optionally the kit may contain one or more means for converting a marker level to a diagnosis of the patient, such as a nomogram, standard table, or computer program for calculating probabilities.

As described in detail in the Examples section the presence or absence of GFAP in a sample strikingly correlates with the presence or absence of intracerebral hemorrhage in the patients investigated. Very importantly it has been found in test samples of patients later proven to suffer from various types of ischemic stroke that at the time of first marker assessment, i.e., within 6 hours after onset of symptoms, none of the samples investigated had an elevated level of GFAP. Thus the analysis for GFAP as performed according to the present invention, in contrast to previous reports based on a state of the art GFAP assay, has a very high specificity for intracerebral hemorrhage. With other words in the cohort investigated no false positive GFAP values have been observed.

GFAP appears to be released almost immediately when hemorrhage sets in and has been found to be elevated for at least 24 hours. GFAP may also be found in the circulation in patients suffering from other types of stroke, like ischemic stroke. However, the release of GFAP in the patients with ischemic stroke follows a completely different time course. Measurable levels of GFAP are found in a sample taken from these patients in the vast majority of cases not within the first 6 hours after stroke onset. It is therefore preferred that the analysis for GFAP in a test sample is performed within the time-frame of 6 hours after on-set of disease. Our findings thus indicate that GFAP—if measured early after onset of disease—may be used as a stand-alone marker to aid in classification of different types of stroke and its presence in a test sample is a clear indicator of intracerebral hemorrhage.

Modern therapeutic approaches like thrombolysis in ischemic stroke are strictly limited to a 6 hour time window. As mentioned, GFAP distinguishes between ischemic stroke and intracerebral hemorrhage in the acute phase of the disease. Thus, this invention will help to guide physicians assessing acute stroke patients to select further appropriate diagnostics.

Moreover, the methods and compositions of the present invention can also be used to facilitate the most appropriate mode of treatment for stroke patients and the development of additional diagnostic and/or prognostic indicators.

The data established also indicate that the severity of hemorrhagic stroke is correlated to the level of GFAP measured. It is therefore also possible and represents a preferred embodiment of the present invention to correlate the level of GFAP to the severity of intracerebral hemorrhage.

Since severity of stroke is also correlated to outcome it is further preferred to correlate the level of GFAP to the disease outcome in a case of intracerebral hemorrhage.

The following examples, references, and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

Antibodies/Antibody Derivatives Used for Measurement of GFAP

With the exception of the blocking antibodies, all immunological reagents have been modified according to one of the following procedures. All antibodies used are commercially available, details/sources are given in detail below.
a) Biotinylation of monoclonal antibody MAB<GFAP>4A11 (Research Diagnostics Inc., catalogue number GFAPabm-411)

The purified antibody preparation comprising MAB<GFAP>4A11 was dialysed against the biotinylation buffer (50 mM KPO$_4$, 100 mM NaCl, pH 8.5) and afterwards the solution was adjusted to a protein concentration of 0.5 mg/ml. D-biotinoyl-aminocaproic acid-N-hydroxysuccinimide ester was dissolved in DMSO and added to the antibody solution in a molar ratio of 1:5. The reaction was stopped by adding L-lysine and the surplus of the labelling reagent was removed by dialysis.

b) Ruthenylation of PAB<GFAP>R-IgG, (DAKO-Cytomation, Catalogue-Nr. Z0334)

The antibodies were dialysed against the ruthenylation buffer (50 mM KPO$_4$, 100 mM NaCl, pH 8.5) and then the solution was adjusted to a protein concentration of 5.4 mg/ml. Ruthenium(II) tris(bipyridyl)-N-hydroxysuccinimide ester was dissolved in DMSO and added to the antibody solution in a molar ratio of 1:2. The reaction was stopped by adding L-lysine and the surplus of the labelling reagent was removed by dialysis or gel permeation chromatography on Sephadex 25.

c) Digoxigenylation of PAB<GFAP>R-IgG

The antibody preparation, PAB<GFAP>R-IgG (DAKO-Cytomation, catalogue-nr. Z0334) was dialysed against the digoxigenylation buffer (50 mM KPO4, 100 mM NaCl pH 8.5) and then the solution was adjusted to a protein concentration of 5.4 mg/ml. Digoxigenin-3-CME-N-hydroxysuccinimide ester was dissolved in DMSO and added to the antibody solution in a molar ratio of 1:5. The reaction was stopped by adding L-lysine and the surplus of the labelling reagent was removed by dialysis.

Example 2

Measurement of GFAP in a Patient Sample

Two assay formats have successfully been used in measurement of GFAP. Details are given below.

a) Microtiter plate assay

Wells of streptavidin-coated microtiter plates (RDG, catalogue nr. 148 705 1001) were incubated with 100 µl/well phosphate buffered saline with 0.05% TWEEN-20 (Polysorbate 20) (PBS-T) and with 1% bovine serum albumin (BSA) containing 1 ng/ml biotinylated IgG of MAB 4A11 (see Example 1a). Incubation was performed for 60 mM at room temperature under shaking.

Wells were washed 4 times with the washing buffer PBS-T.

The incubation with native antigen in patient plasma, diluted in PBS-T buffer, was carried out with 100 µl/well for 1 hour at room temperature under shaking.

Wells were washed 4 times with the washing buffer PBS-T.

The incubation with PAB<GFAP>R-IgG-digoxigenylated (cf. Example 1c) was performed with 100 µl/well PBS-T containing 8 µg/ml digoxigenylated PAB and 1% BSA for 1 hour at room temperature under shaking.

Wells were washed 4 times with the washing buffer PBS-T.

Incubation with 100 µl/well of the detection antibody PAB <Dig>S-IgG-peroxidase conjugate (100 mU/ml; RDG catalogue nr. 1633716) in phosphate buffered saline with 0.05% TWEEN 20 (Polysorbate 20) with 1% BSA took place for 1 hour at room temperature under shaking.

Wells were washed 4 times with the washing buffer PBS-T.

The peroxidase activity was determined in the usual way (in our example using ABTS as a substrate for 30 minutes at room temperature, the extinction difference was read in mU, e.g. at 405 nm for ABTS by means of an ELISA reader).

b) Measurement of GFAP in a Patient Sample on an ELECSYS System Immunoassay Analyzer For measurement of GFAP in human serum or plasma, also a sandwich assay based on chemiluminescence detection was developed and adapted to the requirements of the automated immunoassay instrument ELECSYS from Roche Diagnostics. For the capturing of the antigen biotinylated MAB 4A11 was used (cf. Example 1a). The detection was performed with ruthenylated IgG of PAB<GFAP>Ru (cf. Example 1b).

In the first step the instrument mixes 20 µl of a pre-treatment solution with 50 µl sample and incubates the mixture for 9 min at 37° C. By working with two different pre-treatment solutions for every sample the unspecific signal background for each sample was identified. The first pre-treatment solution contains only phosphate buffered saline with 0.05% TWEEN 20 (Polysorbate 20) and with 1% BSA. The second pre-treatment solution contains 17 µg/ml unmodified MAB 4A11 in phosphate buffered saline with 0.05% TWEEN 20 (Polysorbate 20) and with 1% BSA. The second format is also referred to as "blocked" format further below.

In the second step 40 µl SA-coated paramagnetic beads (720 µg/ml) and 40 µl biotinylated MAB 4A11 (3.2 µg/ml) in phosphate buffered saline with 0.05% TWEEN 20 (Polysorbate 20) and with 1% BSA were added to the mixture from the first step.

Incubation was performed for 9 min at 37° C.

In the third step 40 µl ruthenylated IgG of PAB<GFAP>Ru in phosphate buffered saline with 0.05% TWEEN 20 (Polysorbate 20) and with 1% BSA was added and the mixture was incubated for 9 min at 37° C.

At the end of the incubation the automatic analyzer transfers an aliquot of the mixture to a magnetic field, where the paramagnetic beads are retained, while the un-bound ruthenylated IgG of PAB<GFAP>Ru is not. During measurement excitation of the Ruthenium complex bound to the second antibody leads to the generation of chemiluminescence, that is proportional to the amount of complex bound. The signal generated translates to the amount of analyte plus unspecific background in the sample treated with the first pre-treatment solution and to unspecific background in the sample treated with the second pre-treatment solution.

The difference between the tests with and without unmodified MAB 4A11 in the pre-treatment solution is proportional to the amount of analyte in the sample. This method is mainly important for the detection of very small amounts of analyte in a sample. By using this sample-specific back-ground subtraction a variation in the unspecific background between different samples does not influence the accuracy of the test. Samples containing higher analyte concentrations can be determined without this correction.

Aside from the methodological way to reduce the non-specific background used above, improvements in assay design are now feasible, which will not require any background subtraction, e.g. by use of an improved incubation buffer or antibodies or antibody fragments causing less background. It is obvious to the skilled artisan that improved GFAP assay procedures are now feasible which will be easy to perform.

Suited positive standards in a GFAP-assay are positive samples (e.g. serum, cerebrospinal fluid or brain homogenate) that are diluted in GFAP negative serum or in another diluent to the GFAP concentration required and are then used as a positive standard, whereas a GFAP negative serum or diluent can be used as negative standard.

Example 3

Analytical and Clinical Data as Measured in the ELECSYS Assay

TABLE 1

21-fold determination of a negative and a positive serum (blocked/normal format)

| sample | test | Val 1 | Val 2 | Val 3 | Val 4 | Val 5 | Val 6 | Val 7 | Unit | Number | Average | STDEV | CV | Specific counts |
|---|---|---|---|---|---|---|---|---|---|---|---|---|---|---|
| pos. serum | normal | 2783 | 2711 | 2706 | 2730 | 2620 | 2749 | 2720 | Counts | 21 | 2719 | 45 | 1.66% | 1084 |
|  |  | 2731 | 2730 | 2745 | 2724 | 2772 | 2760 | 2715 |  |  |  |  |  |  |
|  |  | 2719 | 2753 | 2711 | 2671 | 2591 | 2728 | 2730 |  |  |  |  |  |  |
|  | blocked | 1645 | 1667 | 1630 | 1593 | 1631 | 1681 | 1645 | Counts | 21 | 1635 | 25 | 1.56% |  |
|  |  | 1611 | 1621 | 1615 | 1653 | 1625 | 1592 | 1659 |  |  |  |  |  |  |
|  |  | 1615 | 1621 | 1613 | 1646 | 1682 | 1650 | 1648 |  |  |  |  |  |  |
| neg. serum | normal | 1643 | 1643 | 1641 | 1633 | 1629 | 1638 | 1618 | Counts | 21 | 1630 | 14 | 0.85% | 27 |
|  |  | 1628 | 1642 | 1639 | 1652 | 1611 | 1613 | 1622 |  |  |  |  |  |  |
|  |  | 1593 | 1631 | 1648 | 1622 | 1631 | 1628 | 1628 |  |  |  |  |  |  |
|  | blocked | 1616 | 1610 | 1625 | 1567 | 1622 | 1583 | 1605 | Counts | 21 | 1603 | 22 | 1.40% |  |
|  |  | 1602 | 1620 | 1620 | 1621 | 1592 | 1590 | 1563 |  |  |  |  |  |  |
|  |  | 1581 | 1649 | 1599 | 1617 | 1563 | 1611 | 1605 |  |  |  |  |  |  |

TABLE 2

Results as obtained with the GFAP calibrators used

Standards: CSF-Sample diluted in ELECSYS „Universaldiluent"

| | Test format | Val 1 | Val 2 | Number | Average | Std. Dev. | CV | Specific counts |
|---|---|---|---|---|---|---|---|---|
| 1:50000 UD (169 pg/ml) | blocked | 1743 | 1756 | 2 | 1750 | 9 | 0.50% |  |
| 1:50000 UD (169 pg/ml) | normal | 6109 | 6212 | 2 | 6161 | 73 | 1.18% | 4411 |
| 1:100000 UD (84.5 pg/ml) | blocked | 1785 | 1765 | 2 | 1775 | 14 | 0.79% |  |
| 1:100000 UD (84.5 pg/ml) | normal | 3790 | 3809 | 2 | 3800 | 14 | 0.36% | 2025 |
| 1:200000 UD (42.25 pg/ml) | blocked | 1716 | 1777 | 2 | 1746 | 43 | 2.47% |  |
| 1:200000 UD (42.25 pg/ml) | normal | 2870 | 2923 | 2 | 2897 | 38 | 1.31% | 1150 |
| 1:400000 UD (21.13 pg/ml) | blocked | 1732 | 1751 | 2 | 1741 | 13 | 0.76% |  |
| 1:400000 UD (21.13 pg/ml) | normal | 2384 | 2358 | 2 | 2371 | 18 | 0.78% | 630 |
| 1:800000 UD (10.57 pg/ml) | blocked | 1744 | 1747 | 2 | 1746 | 2 | 0.13% |  |
| 1:800000 UD (10.57 pg/ml) | normal | 2062 | 2033 | 2 | 2048 | 20 | 1.00% | 302 |
| 1:1600000 UD (5.28 pg/ml) | blocked | 1752 | 1754 | 2 | 1753 | 1 | 0.08% |  |
| 1:1600000 UD (5.28 pg/ml) | normal | 1963 | 1994 | 2 | 1979 | 22 | 1.11% | 226 |
| ELECSYS Universaldiluent | blocked | 1736 | 1775 | 2 | 1756 | 28 | 1.57% |  |
| ELECSYS Universaldiluent | normal | 1774 | 1763 | 2 | 1768 | 8 | 0.43% | 12 |

TABLE 3

Results of determination of GFAP concentration in serum of 64 well-characterized stroke patients All consecutive patients (n = 64)

| | Intracerebral hemorrhage | Ischemic stroke | ROC-Analysis | |
|---|---|---|---|---|
| GFAP ≥ 3 pg/ml | 13 | 0 | sensitivity | 0.65 |
| GFAP < 3 pg/ml | 7 | 44 | specificity | 1.00 |
| | | | positive predictive value (PPV) | 1.00 |
| | | | negative predictive value (NPV) | 0.86 |

TABLE 4

The results of determination of GFAP concentration in serum of sub-set of 58 well-characterized stroke patients, presenting with moderate to severe neurological deficits Patients with a moderate to severe neurological deficit (n = 58)

| | Intracerebral hemorrhage | Ischemic stroke | ROC-Analysis | |
|---|---|---|---|---|
| GFAP ≥ 3 pg/ml | 12 | 0 | Sens | 0.86 |
| GFAP < 3 pg/ml | 2 | 40 | Spec | 1.00 |
| | | | PPV | 1.00 |
| | | | NPV | 0.95 |

As illustrated in the above Table 3 the accuracy measures indicating intracerebral hemorrhage or cerebral ischemia, respectively, in a patient cohort of n=64 acute stroke patients are very promising. All samples had been obtained within 6 hours after symptom onset and are classified according to a GFAP level of above or equal to 3 pg/ml versus a GFAP level below that threshold.

Figure 2:
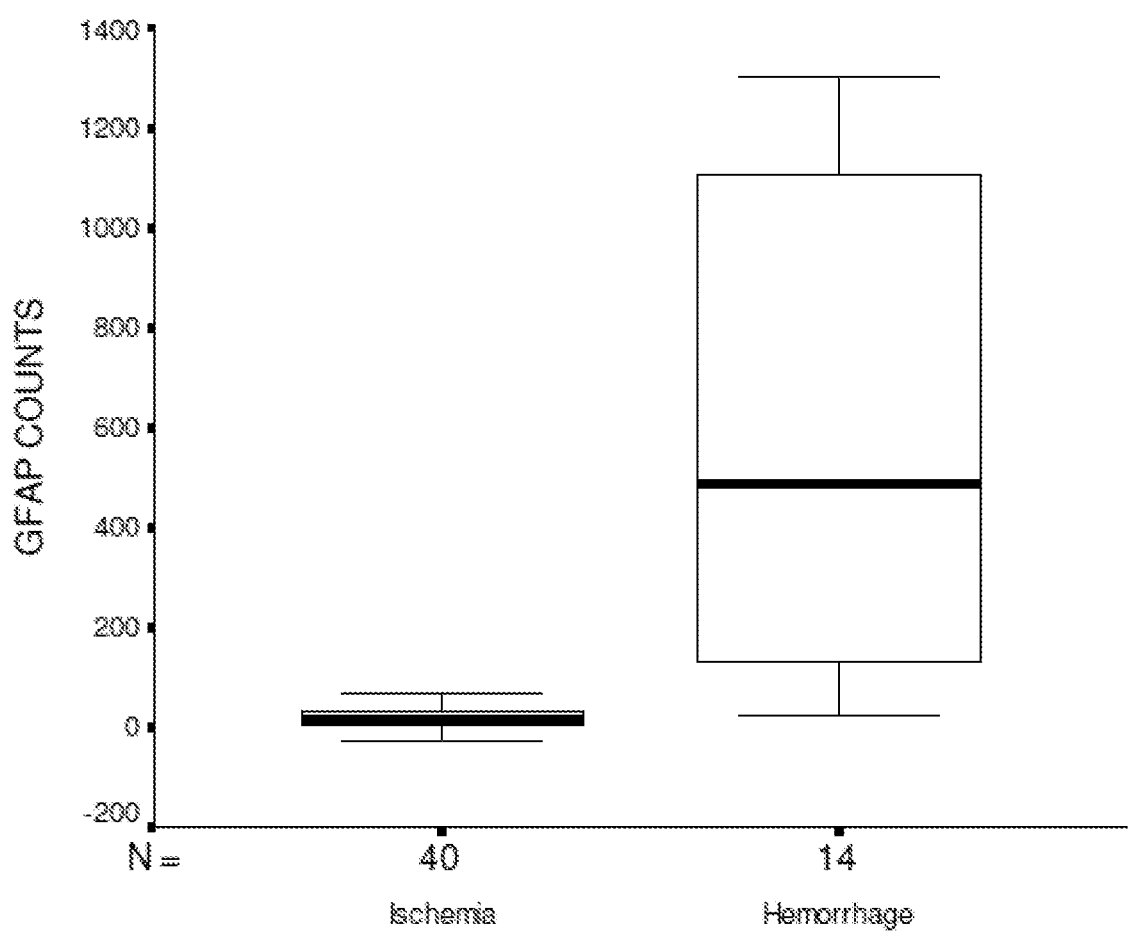
FIG. 2: Distribution of GFAP values as measured in 54 patients with moderate to severe neurological deficits after stroke. Box plots providing GFAP counts (raw data as measured in the ELECSYS analytical system, Roche Diagnostics GmbH) from patients with ischemic stroke and patients with intracerebral hemorrhage, respectively, revealing moderate to severe neurological findings are shown.

Patients with a moderate to severe neurological deficit, were classified according to NIHSS criteria as having a stroke score of four and above (Duncan, P. W., et al., Stroke, 31 (2000) 1429-1438). The corresponding cut-off point 3 pg/ml was derived from receiver-operator characteristic curve analyses (cf. FIG. 1). It is obvious from table 4 that measurement of GFAP in samples obtained from these patients reveals both an excellent PPV as well as NPV. The extremely good discriminatory power of GFAP for separating patients with intracerebral hemorrhage from patients with ischemic stroke is also obvious from FIG. 2.

What is claimed is:

1. A method of treating a stroke patient, the method comprising the steps of:
   detecting whether Glial Fibrillary Acidic Protein (GFAP) is present in a blood or serum sample obtained from the patient within six hours after onset of a stroke by contacting, in vitro, a portion of the blood or serum sample with a detection antibody having specific binding affinity for GFAP and detecting a complex formed between the detection antibody and GFAP; and
   treating the patient with an intracerebral hemorrhage-specific therapy if the presence of GFAP is detected or treating the patient with an ischemic stroke-specific therapy if the presence of GFAP is not detected.

2. The method of claim 1, wherein the ischemic stroke-specific therapy of said step of treating comprises thrombolysis.

3. The method of claim 1, wherein the complex between the detection antibody and GFAP is separated with a capture antibody having specific binding affinity for an epitope of GFAP different that the epitope of GFAP recognized by the detection antibody, the capture antibody being coupled to a solid support.

4. The method of claim 3, wherein the solid support comprises one of a bead and a microwell.

5. The method of claim 3, wherein the solid support comprises a test strip.

* * * * *